(12) United States Patent
Cho et al.

(10) Patent No.: US 9,492,630 B2
(45) Date of Patent: Nov. 15, 2016

(54) WEARABLE COMPUTING DEVICE AND USER INTERFACE METHOD

(71) Applicant: LG ELECTRONICS INC., Seoul (KR)

(72) Inventors: Eunhyung Cho, Seoul (KR); Sinae Chun, Seoul (KR); Jongho Kim, Seoul (KR); Jihwan Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 291 days.

(21) Appl. No.: 14/167,555

(22) Filed: Jan. 29, 2014

(65) Prior Publication Data

US 2015/0092050 A1    Apr. 2, 2015

(30) Foreign Application Priority Data

Sep. 30, 2013    (KR) .................. 10-2013-0116709

(51) Int. Cl.
| | |
|---|---|
| *A61M 21/02* | (2006.01) |
| *A61B 5/0482* | (2006.01) |
| *G08B 21/06* | (2006.01) |
| *A61B 5/00* | (2006.01) |
| *A61B 5/18* | (2006.01) |
| *A61M 21/00* | (2006.01) |

(52) U.S. Cl.
CPC ............ *A61M 21/02* (2013.01); *A61B 5/0077* (2013.01); *A61B 5/0482* (2013.01); *A61B 5/18* (2013.01); *A61B 5/6803* (2013.01); *A61B 5/7405* (2013.01); *G08B 21/06* (2013.01); *A61B 5/4809* (2013.01); *A61M 2021/005* (2013.01); *A61M 2021/0027* (2013.01); *A61M 2021/0083* (2013.01); *A61M 2205/332* (2013.01); *A61M 2205/3306* (2013.01); *A61M 2205/3331* (2013.01); *A61M 2205/3358* (2013.01); *A61M 2205/3375* (2013.01); *A61M 2205/507* (2013.01); *A61M 2230/62* (2013.01); *A61M 2230/63* (2013.01)

(58) Field of Classification Search
CPC ................. A61B 5/18; A61B 5/4809; A61M 2205/507; G08B 21/06
See application file for complete search history.

(56) References Cited

U.S. PATENT DOCUMENTS

| | | | |
|---|---|---|---|
| 2004/0233060 | A1 | 11/2004 | Mohri |
| 2008/0062297 | A1 | 3/2008 | Sako et al. |
| 2009/0018419 | A1* | 1/2009 | Torch ............... A61B 3/0066 600/318 |
| 2010/0214105 | A1 | 8/2010 | Manotas, Jr. |
| 2011/0216181 | A1 | 9/2011 | Yoda et al. |

FOREIGN PATENT DOCUMENTS

| | | |
|---|---|---|
| EP | 0 424 582 A1 | 5/1991 |
| KR | 10-2008-0040378 A | 5/2008 |

(Continued)

*Primary Examiner* — Andy Rao
*Assistant Examiner* — Tyler Edwards
(74) *Attorney, Agent, or Firm* — Birch, Stewart, Kolasch & Birch, LLP

(57) ABSTRACT

There are disclosed a wearable computing device and a method for a user interface. The wearable computing device includes a drowsiness detection unit configured to detect a user's drowsiness; a controller configured to determine whether a current situation corresponds to a first mode not allowing the user's drowsiness or a second mode allowing the user's drowsiness when the user's drowsiness is detected; and a feedback output unit configured to provide the user with at least one feedback comprising a message of the first mode or the second mode according to the mode determined by the controller, wherein the message of the first mode is to fight off the drowsiness and wherein the message of the second mode is to help the user's sleep.

20 Claims, 11 Drawing Sheets

(56) References Cited

FOREIGN PATENT DOCUMENTS

| KR | 20080040378 | A | * | 5/2008 |
| KR | 10-2009-0124333 | A | | 12/2009 |
| KR | 20090124333 | A | * | 12/2009 |
| KR | 10-2010-0133070 | A | | 12/2010 |

* cited by examiner

WEARABLE COMPUTING DEVICE AND USER INTERFACE METHOD

Pursuant to 35 U.S.C. §119(a), this application claims the benefit of earlier filing date and right of priority to Korean Application No. 10-2013-0116709, filed on Sep. 30, 2013, the contents of which are hereby incorporated by reference herein in their entirety.

BACKGROUND OF THE DISCLOSURE

Field of the Disclosure

The present specification relates to a wearable computing device which may be put on at least one body part of a user, more particularly, a wearable computing device which may be put on a human face and a user interface method associated with sleepiness in the face wearable computing device.

Discussion of the Related Art

Among wearable computing devices, a wearable computing device which can be put on a human head or face is referred to as "Head Mounted Display (HMD)" or "Face Mounted Display (FMD).

Such a wearable computing device may be combined with augmented reality technology and N screen technology and provide various conveniences to a user.

In addition, the wearable computing device may be used in connection with various external digital devices. Such the wearable computing device implements communication with the various external digital devices to receive a user input for a corresponding external digital device or to perform works in communication with a corresponding external digital device.

(a), (b), (c) and (d) of FIG. 1 show examples of the wearable computing device configured to be put on a user's head or face. As shown in (a), (b), (c) and (d) of FIG. 1, there are a variety of wearable computing devices and any types of wearable computing devices may be applied to the present disclosure. For example, a glass type computing device shown in (a) of FIG. 1, a sunglass type computing device shown in (b) of FIG. 1 and a hair-band type computing device may be applicable.

The wearable computing device shown in (a), (b), (c) and (d) of FIG. 1 provides images and/or sounds to a user, using a display and/or a speaker. Especially, a small-sized display device (e.g., a liquid crystal display) provided in the wearable computing device is typically arranged adjacent to at least one of eyes and the wearable computing device projects an image to the display device.

SUMMARY OF THE DISCLOSURE

Exemplary embodiments of the present disclosure provide a wearable computing device which may warn a user's sleepiness or help sound sleep in accordance with a situation determined whether the user is allowed to sleep once sensing the user's sleepiness and a user interface method of the same.

To achieve these objects and other advantages and in accordance with the purpose of the present specification, as embodied and broadly described herein, a wearable computing device may include a drowsiness detection unit configured to detect a user's drowsiness, a controller configured to determine whether a current situation corresponds to a first mode not allowing the user's drowsiness or a second mode allowing the user's drowsiness when the user's drowsiness is detected, and a feedback output unit configured to provide the user with at least one feedback comprising a message of the first mode or the second mode according to the mode determined by the controller. Herein, the message of the first mode is to fight off the drowsiness and the message of the second mode is to help the user's sleep.

The drowsiness detection unit may detect the user's drowsiness, using at least one of the user's eye blinking, the user's eye closing time, a state of the user's eyes, the user's pulsation, the user's brainwave, the user's body temperature and a line of the user's vision.

The wearable computing device may further include a Global Positioning System (GPS) unit configured to receive location information of the wearable computing device from one or more GPSs, and a camera unit configured to capture images in a range corresponding to the user's line of vision and/or images of the user's surrounding, using one or more cameras.

The controller may determine whether the user is driving using one or more of the images captured by the camera unit, the location information received from the GPS unit and information sensed by one or more sensor, and the controller may determine that the current situation is corresponding to the first mode when the user is driving based on the result of the determination.

The controller may detect the user's location and place using one or more of the images captured by the camera unit, the location information received from the GPS unit and the information sensed by one or more sensors when the user is not driving based on the result of the determination, and the controller may determine whether the current situation corresponds to the first mode or the second mode based on the detected location and place.

The first mode and the second mode may be manually using at least one of a button, a menu and a voice command provided in the wearable computing device.

The at least one feedback comprising the message of the first mode may comprise at last one of a first audio feedback, a first alarm feedback, a first video feedback and a first brainwave feedback, and the at least one feedback comprising the message of the second mode may comprise at least one of a second audio feedback, a second alarm feedback, a second video feedback and a second brainwave feedback.

The feedback output unit may comprise an audio output unit configured to output one of the first audio feedback and the second audio feedback based on the control of the controller, an alarm output unit configured to output one of the first alarm feedback and the second alarm feedback based on the control of the controller, a display unit configured to output one of the first video feedback and the second video feedback based on the control of the controller, and a brainwave output unit configured to output one of the first brainwave feedback and the second brainwave feedback based on the control of the controller.

The feedback provided to the user by the feedback output unit to fight off the drowsiness and the message of the first mode included in the feedback may be determined by learning of the wearable computing device.

The feedback provided to the user by the feedback output unit to fight off the drowsiness and the message of the first mode included in the feedback may be determined by the user.

The feedback provided to the user by the feedback output unit to help the user's sleep and the message of the second mode included in the feedback may be determined by learning of the wearable computing device.

The feedback provided to the user by the feedback output unit to help the user's sleep and the message of the second mode included in the feedback may be determined by the user.

The controller may control a brightness of lighting near the user based on whether the current situation corresponds to the first mode or the second mode, using a wireless communication function.

The controller may convert a mode of the wearable computing device into a standby mode when the current situation corresponds to the second mode.

The controller may provide the user with a feedback comprising a different message of the first mode when the user's drowsiness is detected after the feedback comprising the message of the first mode is provided to the user for a preset time period.

The controller provides the user with a feedback comprising a different message of the second mode, when the user's sleep is not detected after the feedback comprising the message of the second mode is provided to the user.

The controller may provide the user with the feedback comprising the message of the second mode when a mode conversion is requested by the user while the feedback comprising the message of the first mode is provided to the user.

The controller may provide the user with the feedback comprising the message of the first mode when a mode conversion is requested by the user while the feedback comprising the message of the second mode is provided to the user.

In another aspect, a method of a user interface for a wearable computing device may include detecting whether a user is drowsy, determining whether a current situation corresponds to a first mode not allowing the user's drowsiness or a second mode allowing the user's drowsiness when the user's drowsiness is detected, and providing the user with at least one feedback comprising a message of the first mode or the second mode according to the mode determined in the step. Herein the message of the first mode may be to fight off the drowsiness and wherein the message of the second mode may be to help the user's sleep.

Additional advantages, objects, and features of the present specification will be set forth in part in the description which follows and in part will become apparent to those having ordinary skill in the art upon examination of the following or may be learned from practice of the present specification. The objectives and other advantages of the present specification may be realized and attained by the structure particularly pointed out in the written description and claims hereof as well as the appended drawings.

BRIEF DESCRIPTION OF THE DRAWINGS (a), (b), (c) and (d) of FIG. 1 illustrate embodiments of various wearable computing devices;

DESCRIPTION OF SPECIFIC EMBODIMENTS

Figure 1:
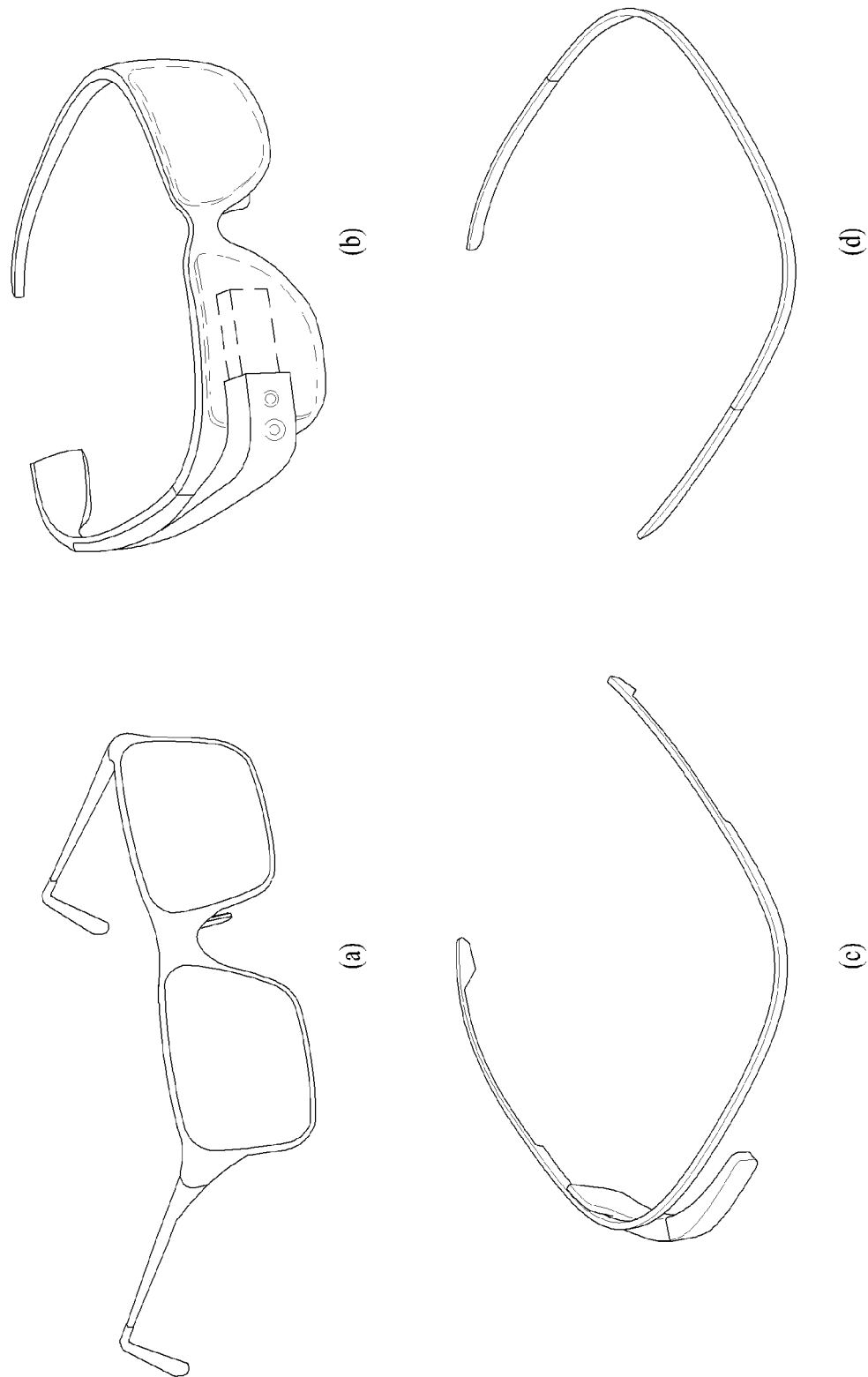

Exemplary embodiments of the disclosed subject matter are described more fully hereinafter with reference to the accompanying drawings. The disclosed subject matter may, however, be embodied in many different forms and should not be construed as limited to the exemplary embodiments set forth herein. Rather, the exemplary embodiments are provided so that this disclosure is thorough and complete, and will convey the scope of the disclosed subject matter to those skilled in the art. In the drawings, the size and relative sizes of layers and regions may be exaggerated for clarity. Like reference numerals in the drawings denote like elements.

It will be understood that when an element or layer is referred to as being "on", "connected to", or "coupled to" another element or layer, it can be directly on, connected, or coupled to the other element or layer or intervening elements or layers may be present. In contrast, when an element is referred to as being "directly on", "directly connected to", or "directly coupled to" another element or layer, there are no intervening elements or layers present. As used herein, the term "and/or" includes any and all combinations of one or more of the associated listed items. It may also be understood that for the purposes of this disclosure, "at least one of X, Y, and Z" can be construed as X only, Y only, Z only, or any combination of two or more items X, Y, and Z (e.g., XYZ, XYY, YZ, ZZ).

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the present disclosure.

The terminology used herein is for the purpose of describing exemplary embodiments only and is not intended to be limiting of the disclosed subject matter. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Exemplary embodiments of the disclosed subject matter are described herein with reference to cross-section illustrations that are schematic illustrations of idealized embodiments (and intermediate structures) of the disclosed subject matter. As such, variations from the shapes of the illustrations as a result, for example, of manufacturing techniques and/or tolerances, are to be expected. Thus, exemplary embodiments of the disclosed subject matter should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this disclosed subject matter belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present disclosure is to detect a user's sleepiness (or drowsiness) by using the wearable computing device and to provide the user with a feedback in accordance with each of situations so as to warn drowsiness or help sleep based on the result of the detecting. Specifically, when the situation does not allow the user to be drowsy, the wearable computing device provides the user with at least one feedback so as to fight off sleepiness. When the situation allows the user to fall asleep, the wearable computing device provides the user with at least one feedback helpful to sleep.

At this point, the feedback is a message type feedback provided to the user with reference to each of the situations. There may be an audio feedback, a visual feedback, an alarm feedback and a brainwave feedback, and so on.

In an embodiment of the present disclosure, each of feedbacks includes two mode messages. For description convenience, the situation not allowing the user's drowsiness may be a first mode and the situation allowing the user's drowsiness may be a second mode. That is for helping the present disclosure understood completely and the reverse of the order may be possible.

In other words, a message for the first mode may include at least one of audio, video, brainwave and alarm feedbacks. A message for the second mode may include at least one of audio, video, brainwave and alarm feedbacks. Two feedbacks corresponding to each mode have two different messages. For example, the audio feedback included in the message for the first mode may be calming music and the audio feedback included in the message for the second mode may be loud music.

In the present disclosure, the message for the first mode is referred to as a message for drowsiness warning and the message for the second mode is referred to as a message for sleep helping.

It is assumed in the present disclosure that the user is putting on the wearable computing device to detect whether or not the user is drowsy, to determine the first/second mode, and to provide the user with a feedback according to the determined mode.

Figure 2:
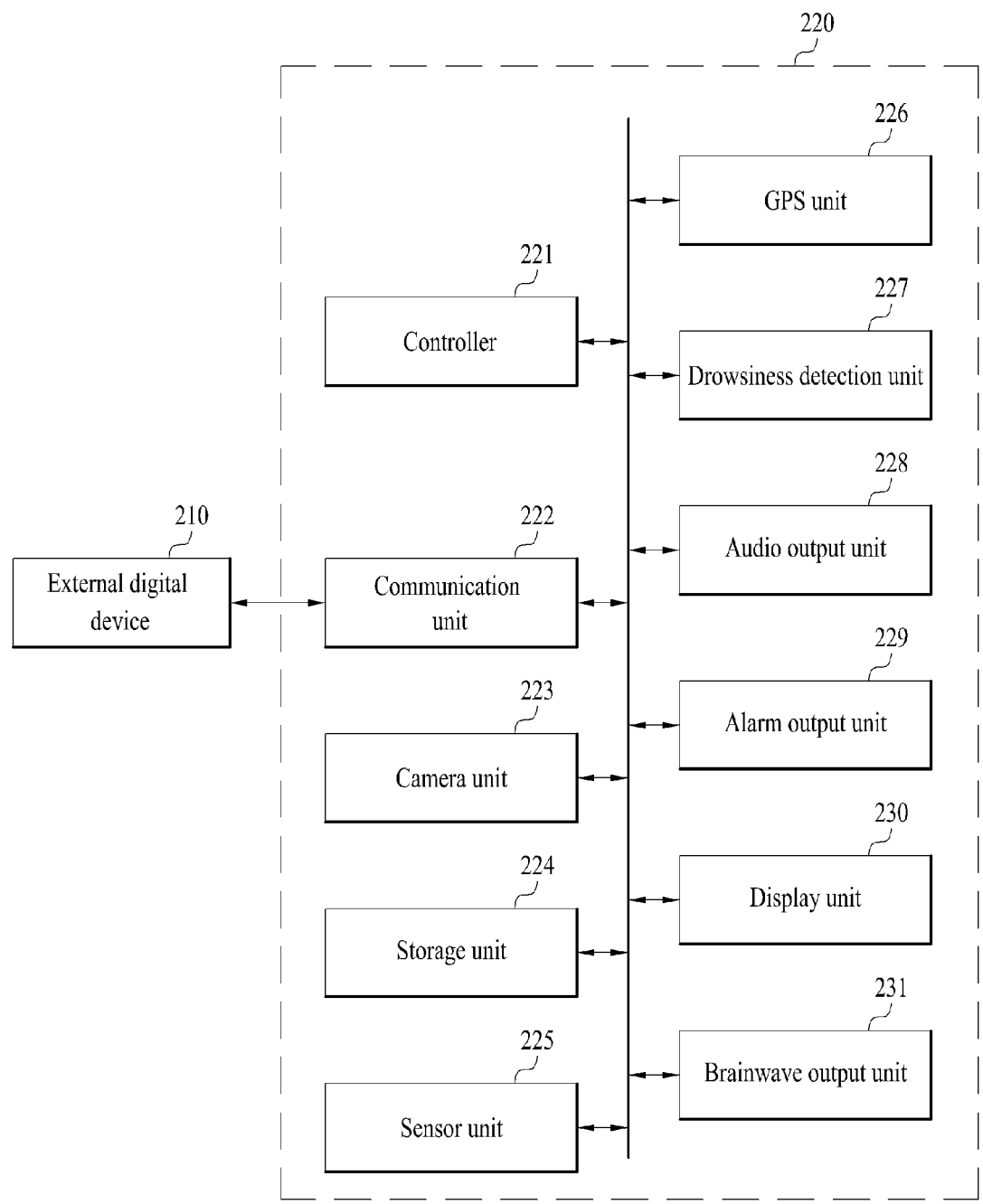
FIG. 2 is a block diagram of a wearable computing device according to exemplary embodiments of the present disclosure.

FIG. 2 is a block diagram of a wearable computing device 220 according to one embodiment of the present disclosure. The wearable computing device 220 may include a controller 221, a communication unit 222, a camera unit 223, a storage unit 224, a sensor unit 225, a GPS unit 226, a drowsiness detection unit 227, an audio output unit 228, an alarm output unit 229 and a display unit 230. The wearable computing device may further include a brainwave output unit 231. One or more external digital devices 210 configured to provide data (e.g., contents) may be connected to the communication unit 222 of the wearable computing device 220 via a wire or wirelessly.

The controller 221 included in the wearable computing device 220 may implement an application (or a program) and process data of the wearable computing device. In addition, the controller 221 may control the communication unit 222, the camera unit 223, the storage unit 224, the sensor unit 225, the GPS unit 226, the drowsiness detection unit 227, the audio output unit 228, the alarm output unit 229 and the display unit 230. The controller 221 may also manage data transmission between two of the units.

According to an embodiment of the present disclosure, the controller 221 checks whether the situation allows the user to be drowsy when the drowsiness detection unit 227 detects the user's drowsiness, and controls one corresponding unit to provide the user with at least one feedback based on the result of the checking.

According to an embodiment of the present disclosure, it is detected by the drowsiness detection unit 227 whether the user is drowsy. However, According to another embodiment of the present disclosure, the user's drowsiness may be detected by the controller 221. In contrast, the drowsiness detection unit 227 may detect whether the user is drowsy and determine whether the situation allows the user's drowsiness when the user's drowsiness is detected. Hence, the drowsiness detection unit 227 may control the corresponding units to provide the user with at least one feedback based on the result of the determination.

The operations of the controller 221 and the drowsiness detection unit 227 may be performed by hardware, a firmware, a middleware or a software or combination of at least two of them.

The communication unit 222 is connected to the external digital device 210 via a wire or wirelessly. Any devices configured to provide the wearable computing device 220 with video/audio data may be the external digital device 210. For example, the external digital device 210 may be a mobile terminal or a fixed terminal. Examples of the mobile terminal may include a cellular phone, a smart phone, a tablet PC (Personal Computer), a smart pad, a notebook, a digital broadcasting terminal, PDA (Personal Digital Assistant), PMP (Portable Multimedia Player), a digital camera or a navigator. Examples of the fixed terminal may include a desk top, DVD (Digital Video Disc or Digital Versatile Disc) player and TV.

The communication unit 222 and the external digital device 210 may transmit/receive data via a wire or wirelessly using various protocols. For example, in case that they transmit/receive data via a wire, HDMI (High Definition Multimedia Interface) or DVI (Digital Visual Interface) may be supported. In case that they transmit/receive data wirelessly, 2G, 3G and 4G mobile communication system interfaces may be supported. Examples of 2G, 3G and 4G mobile communication interfaces may include mobile communication system (e.g., GSM (Global System for Mobile Communication), CDMA (Code Division Multiple Access), Wibro, HSPA (High Speed Packet Access), HSDPA (High Speed Downlink Packet Access), LTE (Long Term Evolution)), Bluetooth, and short range communication systems (e.g., IrDA (Infrared Data Association), UWB (Ultra Wideband), Zigbee, WLAN (Wireless LAN) (WiFi)).

The wire/wireless interface systems are examples for helping the present disclosure understood easily and the interface methods for transmitting/receiving information may be easily modified by people skilled in the art. Accordingly, the interface method according to the embodiments of the present disclosure may not be limited to the embodiments.

The camera unit 223 captures (or photographs or takes) an image near the wearable computing device and converts the captured image into an electric signal. For that, the camera unit 223 may include an image sensor and the image sensor may convert an optical signal into an electric signal. The image converted into the electric signal after captured by the camera unit 223 may be stored in the storage unit 224 before being output to the controller 21 or output to the controller 221 without stored in the storage unit 224. In addition, the camera unit 223 captures an image located in a range corresponding to the user's view and converts the captured image into an electric signal. The converted electric signal is stored in the storage unit 224 and output to the drowsiness detection unit 227, or directly output to the drowsiness detection unit 227 without stored in the storage unit 224. The image captured by the camera unit 223 may be a still image or a motion picture.

Applications (or programs) for the operation of the controller 221 may be stored in the storage unit 224 or the image acquired by the camera unit 223 may be stored in the storage unit 224. Audio data, photographs, video data, applications and various contents may be stored in the storage unit 224.

Examples of the storage unit 224 may include RAM (Random Access Memory), SRAM (Static Random Access Memory), ROM (Read Only Memory), EEPROM (Electrically Erasable Programmable Read Only Memory) and PROM (Programmable Read Only Memory). The wearable computing device 220 may be driven in association with web storage for implementing the storage function of the storage unit 224 on the internet.

The storage unit 224 may further include an external storage media detachably mounted to the wearable computing device 220. The external storage media may be a slot type storage media (e.g., a SD (Secure Digital) memory and a CF (Compact Flash) memory), a memory stick type or USB (Universal Serial Bus). In other words, any storage media demountable from the wearable computing device 220 and configured to provide the wearable computing device with contents (e.g., audio data, photographs, video data and applications) may be provided as the external storage media.

The sensor unit 225 may transmit the environment recognized by the wearable computing device 220 to the controller 221, using a plurality of sensors arranged in the wearable computing sensor 220. At this time, the sensor unit 220 may include a plurality of sensing means. In one embodiment, the plurality of the sensing means may include a gravity sensor, a terrestrial magnetism sensor, a motion sensor, a gyro sensor, an acceleration sensor, an infrared ray sensor, an inclination sensor, a brightness sensor, a height sensor, an olfactory sensor, a temperature sensor, a depth sensor, a pressure sensor, a bending sensor, an audio sensor, a video sensor and a touch sensor.

The pressure sensor of the sensing means may detect whether a pressure is applied to the wearable computing device 220 and the size of the pressure. The pressure sensor module may be provided in any areas of the wearable computing device 220 which require pressure detection according to use environment.

The motion sensor detects the position or movement of the wearable computing device 220. The acceleration sensor used in the motion sensor may be a device configured to convert change in acceleration in one direction into an electric signal and such the acceleration sensor is broadly used together with development of MEMS (Micro-electromechanical Systems). There are many types of acceleration sensors including one type mounted in an air-back system of a vehicle to measure a large value of acceleration used in sensing crash, another type configured to measure a small value of acceleration used as input means of a game and the like by recognizing minute movement of a human hand and other various types. The gyro sensor is a sensor configured to measure an angular velocity and it can sense a direction of rotation with respect to a reference direction.

The sensor unit 225 may further include a brainwave sensor configured to measure a brainwave of the user and to provide the measured brainwave to the drowsiness detection unit 227.

The brainwave sensor measures a brainwave from the user's scalp and outputs the measured brainwave signal to the drowsiness detection unit 227. At this time, the brainwave may be classified into LPF, EcoG and EEG (Electroencephalogram) based on a measuring place and a type of a brainwave. According to an embodiment of the present disclosure, the brainwave sensor may measure an EEG signal generated in the user's scalp.

One or more brainwave sensors may be provided and arranged in an area of the wearable computing device 220 that can contact with the user's scalp.

The infrared ray sensor measures an infrared ray emitted from the user and outputs the measured infrared ray to the drowsiness detection unit 227.

In the embodiments of the present disclosure, the sensor unit 227 may refer to the sensing means mentioned above and sense the user's various input and user environment, to transmit the result of the sensing to the controller 221 such that the controller 221 can implement operations corresponding to the result of the sensing. The sensors mentioned above may be included in the wearable computing device 220 as independent elements or combined into one or more elements.

The GPS (Global Positioning System) unit 226 receives location information of the wearable computing device 220 from a plurality of GPS satellites and provides the received location information to the controller 221.

The drowsiness detection unit 227 detects whether the user is in a drowsy state based on the image captured by the camera unit 223 and/or the result of the sensing performed by the sensor unit 225, and then it outputs the result of the detection to the controller 221.

The drowsiness detection unit 227 may detect whether the user is drowsy using one or more sources. For example, one or more sources may be information on the user's eye blinking, the time when the user is closing the eyes, a state of the user's eyes, pulsation, brainwaves, a temperature, EMG, ECG, EOG and the user's gaze, the drowsiness detection unit 227 may detect the user's drowsiness based on one or more sources.

In one embodiment, the drowsiness detection unit 227 may determine whether the user is drowsy based on the images in a range corresponding to the user's view which are captured by the camera unit 223 and a position of the user's pupil.

In another embodiment, the drowsiness detection unit 227 identifies a bandwidth the user's brainwave signals measured by the brainwave sensor belongs to and detects whether the user is in a drowsy state based on the result of the checked bandwidth. The brainwave generated by electric activity of nerve cells in the cerebral cortex may be categorized into a delta wave (0.5~3.99 Hz), a theta wave (4~7.99 Hz), an alpha wave (8~12.99 Hz), a beta wave (13~29.99 Hz) and a gamma wave (30 Hz or more) based on a bandwidth they belongs to. There can be generated a difference between frequencies according to a state of the brain. In other words, beta waves are more than the others in an arousal state and the alpha waves are more than the others in a state where the mind and body are stabilized or the eyes are closed. The theta waves are more than the others in a state the user enters into a light sleep and the delta waves are more in a state the user enters into a deep sleep state. In a transmission period between an awakening state before sleeping and a sleeping state, the human enters into a mentally stabilized state and the eye-close time is increasing such that the alpha waves can be more than the other waves. The theta waves remains as they were or getting relatively less because of the alpha wave increasing. Such a phenomenon of the theta waves in the awakening state and the sleeping state may be used as a reference of brainwave drowsiness determination. In other words, the bandwidth of the brain waves measured by the brain wave sensor of the sensor unit 225 may be analyzed and the types of the brain waves are figured out based on the result of the analysis. In this instance, it can be determined whether the user is drowsy at the current time. Also, the drowsiness detection unit 227 may determine whether the user is in a sleep state based on the bandwidth of the brainwaves.

In one embodiment, the drowsiness detection unit 227 may detect the user's drowsiness based on the eye blinking information. The eye blinking information includes at least one of an eye-blinking frequency and eye-blinking period. The eye blinking information may be detected from digital information on the user's brain waves measured by the brain wave sensor of the sensor unit 225. Generally, the human eye-blinking frequency per unit time is increasing in a pre-sleep state than in the awakening state and the frequency is drastically decreasing in the sleep state, such that the eye closed time can be increasing. The eye blinking frequency is in inverse proportion to the eye blinking period. Accordingly, the eye blinking period in the pre-sleep state is reducing and the eye blinking period in the sleep state is increasing. When the drowsiness is detected by the eye blinking frequency, the eye blinking frequency has to be calculated with putting it on hold to determine drowsiness and it is difficult to take appropriate steps for the user's drowsiness. When the drowsiness is detected by the eye blinking period, the before eye blinking and the current eye blinking have to be put into consideration and there is one advantage that the user's drowsiness state can be reflected in the drowsiness determining in real time. Accordingly, it is preferred that the eye blinking period is used as the reference of the drowsiness determination. At this time, the characteristic can be used that the eye blinking period is decreasing in the pre-sleep state and increasing in the sleep state.

In one embodiment, the drowsiness detection unit 227 may detect the user's drowsiness based on the user's body temperature calculated from the infrared ray measured by the infrared ray sensor of the sensor unit 225. For example, when the calculated body temperature is lower than the user's average body temperature by a predetermined value or more, it may be determined that the user is drowsy.

In one embodiment, the drowsiness detection unit 227 may detect the user's drowsiness based on both the eye blinking information and the user's brain wave.

The embodiments for detecting the user's drowsiness are disclosed to make the present disclosure understood easily and the user's drowsiness may be detected based on other various sources.

The information on the result of the user's drowsiness detection performed by the drowsiness detection unit 227 may be output to the controller 221.

The controller 221 may determine whether the user is allowed to be drowsy or not allowed to be drowsy, when the user's drowsiness is detected by the drowsiness detection unit 227.

In the present disclosure, the situation where the user is not allowed to be drowsy may be referred to as "a first mode" and the situation where the user is allowed to be drowsy as "a second mode" for convenience sake.

At this time, there are various methods for determining whether the current mode is a first mode or a second mode. In one embodiment, it is determined whether it is the first mode or the second mode, using one or more of the user's movement and location information. For that, the controller 221 may use the images of surroundings captured by the camera unit 223, the location information received from the GPS unit 226 and the sensing information output by the sensor unit 225. For example, when it is determined the user is at the wheel, the mode is set as the first mode which not allows the user to be drowsy. In one embodiment, even when the speed at which the user is moving is corresponding to the speed of the vehicle, it cannot be absolutely determined that the user is at the wheel and it is additionally determined whether the user is at the wheel based on the user's current location the image of the surrounding. Specifically, the user can be moving in a seat not at the wheel or in a bus.

The controller 221 may set the current mode as the first mode or the second mode, once determining that the user is moving not the driving. Even once determining that the user is not moving, the controller 221 may set the mode as the first mode or the second mode based on the user's current location and place. For example, when the user is in a lecture room to take a lecture, the controller 221 determines the current mode as the second first mode not allowing the user to be drowsy. When the user is at home, the controller 221 determines the current mode as the first mode allowing the user to be drowsy. Even in the same condition, it can be the situation not allowing the user's drowsiness or the situation allowing the user's drowsiness. For that, information on various situations categorized for the first mode and the second mode may be provided to a manufacturer or the user to store the information in the storage unit 224. The information may be used in determining whether it is set as the first mode or the second mode. As another example, the mode may be the first mode or the second mode based on the learning of the wearable computing device 220. As a further example, when it is the situation makes it difficult to determine whether the mode is set as the first mode or the second mode, the first mode may be set and feedbacks corresponding to the first mode may be provided to the user. At this time, the user may be change the mode, using a button or a menu.

When detecting the use's drowsiness, the controller 221 mentioned above determines whether the current mode is set as the first mode not allowing the user's drowsiness or the second mode allowing the user's drowsiness, using the various methods and sources mentioned above. After that, the controller controls a corresponding unit to provide the user with at least one feedback corresponding to the determined mode. In other words, when the determined mode is the first mode, the controller provides at least one feedback for shaking off the drowsiness via a corresponding unit. When the determined mode is the second mode allowing the user's drowsiness, the controller provides the user with at least one feedback for helping sound sleep via a corresponding unit.

Here, the feedback is a message type provided to the user according to each of the situations. There may be an audio feedback provided to the user via the audio output unit 227, a visual feedback provided via the display unit 230, an alarm feedback provided via the alarm output unit 229 and a brainwave feedback provided via the brainwave output unit 231.

Especially, in the embodiment of the present disclosure, there may be two mode messages for each of the feedbacks. In other words, a message for the first mode may include one or more of the audio feedback, the video feedback, the brainwave feedback and the alarm feedback. A message for the second mode may also include one or more of the audio feedback, the video feedback, the brainwave feedback, the alarm feedback. Two corresponding feedbacks in each of the modes have a different message. For example, the audio feedback included in the message for the first mode may be calming music and the audio feedback included in the message for the second mode may be loud music.

In the present disclosure, the one or more feedbacks which will be provided to the user according to the determined mode and the message provided by the one or more feedbacks may be preset in the wearable computing device 220 or automatically set by learning, or they may be directly set by the user. In the case where the feedbacks and the message are automatically set by the learning, it is determined that the best effect is achieved when "A" music is output in the first mode as the audio feedback, the audio output unit 228 is controlled to output "A" music as the audio feedback. "A" music may be pre-stored in the storage unit 224 or provided from the external digital device 210.

The audio feedback is described to make the present disclosure understood easily and the audio feedback, the brainwave feedback and the alarm feedback may be provided, similar to the audio feedback.

The audio output unit 228 outputs an audio signal of the contents implemented in the wearable computing device 220. The contents may be provided from the storage unit 224 or the external digital device 210. Also, the contents may be provided from the camera unit 223.

The audio output unit 228 may include one or more of an air conduction speaker and a bone conduction speaker.

The bone conduction speaker may be arranged in various positions for providing an audio signal converted into frequency type vibration. When using the bone conduction speaker, the audio signal drives the bone conduction speaker and a bone conduction sound wave is conduced to the user's skull and the frequency type vibration is transmitted to the user. When using the bone conduction speaker, the user can hear the audio signal without damage to the eardrum.

Examples of the air conduction speaker include an earphone. The air conduction generates a sound wave by vibrating air according to an audio signal. In other words, the vibration of the sound transmitted to the air may be transmitted to the eardrum in the user's ear and the vibration of the eardrum is transmitted to a screw-shaped cochlea via three bones located in the eardrum. The cochlea is filled with lymph fluid and vibration of the lymph fluid is converted into an electric signal and transferred to the auditory nerve, such that a human brain can recognize sound.

The audio output unit 228 may output the audio feedback of the first mode to warn the drowsiness or the audio feedback of the second mode to help sound sleep according to the control of the controller 221.

Examples of the message provided by the audio feedback of the first mode may include a loud music or song, a loud noise, a voice of the person who the user is afraid of or dislikes (e.g., the user's superior), a specific signal sound. The mention like "Don't be drowsy" or "Wake up" made by the person the user usually dislikes or fears may be used.

Examples of the message provided by the audio feedback of the second mode may include a calming music or song and a sound of the nature.

When an event requiring notification to the user is generated, the alarm output unit 229 may transmit notification to the user, using an alarm. The alarm may be a tactile feedback or vibration. The tactile feedback unit uses ultrasonic vibrations and it can control a vibration frequency and a vibration size.

The alarm output unit 229 may output an alarm feedback of the first mode for warning drowsiness or an alarm feedback of the second mode for helping sound sleep according to the control of the controller 221.

A message provided by the alarm feedback of the first mode may be a tactile feedback which gives a sting sensation to the user to fight off the drowsiness.

A message provided by the alarm feedback of the second mode may be a tactile feedback which gives a soft sensation to the user to help sound sleep.

The display unit 230 output a video signal of the contents implemented in the wearable computing device 220. The contents may be provided by one of the external digital device 220, the camera unit 223 and the storage unit 224. Examples of the display unit 230 may include a liquid crystal display, a thin film transistor liquid crystal display, a light emitting diode, an organic light emitting diode, a flexible display and 3D display. Also, the examples of the display unit 230 may include the air and transparent glass. In other words, any materials capable of visually transmitting the video signal to a person may be the display unit 230.

The display unit 230 may output a video feedback of the first mode for warning drowsiness or a video feedback of the second mode for helping sound sleep according to the control of the controller 221.

Examples of a message provided by the video feedback of the first mode may include a flashy painting, a photograph and a motion picture for shaking off the drowsiness.

Examples of a message provided by the video feedback of the second mode may include a painting, a calming scenery photograph and a motion picture for helping sound sleep.

The brain wave output unit 231 may output a brain wave feedback of the first mode for warning the drowsiness or a brain wave feedback of the second mode for helping the sound sleep according to the control of the controller 221.

Examples of a message provided by the brain wave feedback of the first mode may include an alpha wave in frequency bandwidth range of 8 Hz~13 Hz to fight off drowsiness.

Examples of a message provided by the brain wave feedback of the second mode may include a theta wave in a frequency bandwidth range of 4 Hz~7 Hz to help sound sleep.

Figure 3:
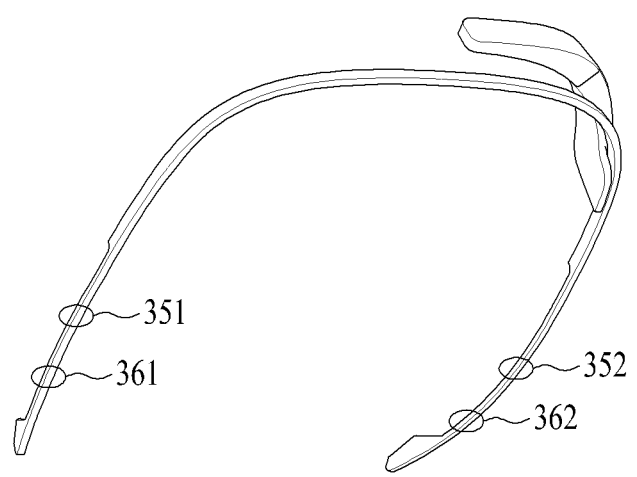
FIG. 3 illustrates a wearable computing device which includes a brainwave sensor and a vibrator according to one embodiment of the present disclosure.

FIG. 3 is a wearable computing device according to one embodiment of the present disclosure. Brain wave sensors 351 and 352 for measuring a brain wave and vibrators 361 and 362 may be arranged in both legs of the wearable computing device, respectively. The arrangement is one of embodiments and they may be any portions of the wearable computing device which can measure the user's brain wave and transmit vibration to the user. The number of the brain wave sensors and the number of the vibrators are one of the embodiments to help the present disclosure understood easily and the present disclosure is not limited to the embodiment mentioned above.

Figure 4:
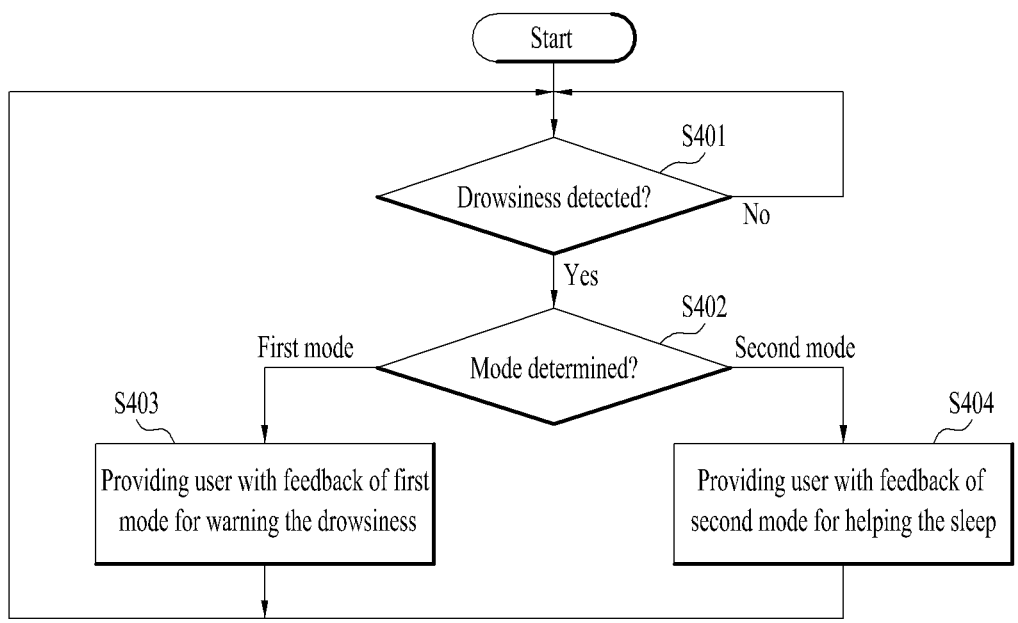
FIG. 4 is a flow chart illustrating a user interface method of the wearable computing device according to an embodiment of the present disclosure.

FIG. 4 is a flow chart of a user interface according to one embodiment for the wearable computing device.

Once the user's drowsiness of detected (S401), it is determined whether the current situation is corresponding to the first mode not allowing the user's drowsiness or the second mode allowing the user's drowsiness (S402). The method of detecting the user's drowsiness and the method of determining the mode are described in detail above and omitted accordingly.

When the current mode is determined as the first mode in the step of S402, the feedback of the first mode for warning the drowsiness is provided to the user (S403). The feedback of the first mode may be one of the audio feedback, the video feedback, the alarm feedback and the brain wave feedback. At this time, the message provided by each of the feedbacks is described in detail above and omitted accordingly.

When the current mode is determined as the second mode, the feedback of the second mode for helping the user's sound sleep is provided to the user (S404). The feedback of the second mode may be one of the audio feedback, the video feedback, the alarm feedback and the brain wave feedback. At this time, the message provided as each of the feedbacks is described in detail above and omitted accordingly.

Figure 5:
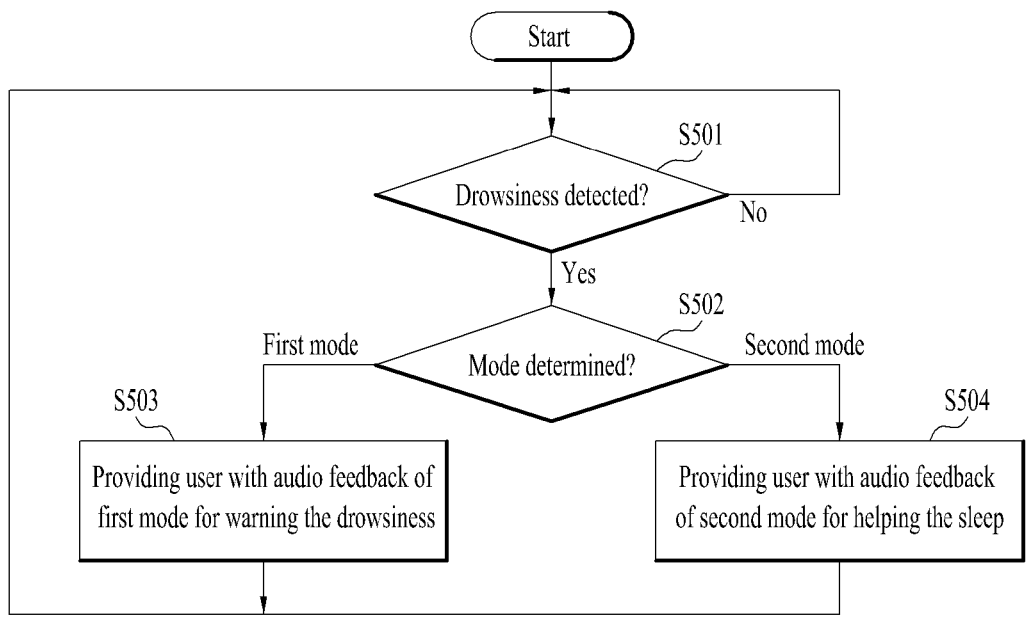
FIG. 5 is a flow chart illustrating a user interface method of the wearable computing device according to another embodiment of the present disclosure.

FIG. 5 is a flow chart of a user interface according to another embodiment of the wearable computing device, especially, a flowchart when the feedback provided to the user is the audio feedback.

Specifically, once the user's drowsiness is detected (S501), it is determined whether the current situation is corresponding to the first mode not allowing the user's drowsiness or the second mode allowing the user's drowsiness (S502). The method of detecting the user's drowsiness and the method of determining the mode are described in detail above and omitted accordingly.

When the current mode is determined as the first mode in the step of S502, the audio feedback of the first mode for warning the drowsiness is provided to the user (S503). The message provided by the audio feedback of the first mode may be the loud music or song, the loud sound, the voice of the person the user usually dislikes or fears (e.g., a boss) or the specific signal sound to fight off the drowsiness. At this time, the mention like "Don't be drowsy" or "Wake up" made by the person the user usually dislikes or fears may be used.

When the current mode is determined as the second mode in the step of S502, the audio feedback of the second mode for helping the user's sound sleep is provided to the user (S504). The message provided by the audio feedback of the second mode may be the calming music or song or the sound of the nature for helping the sound sleep.

Figure 6:
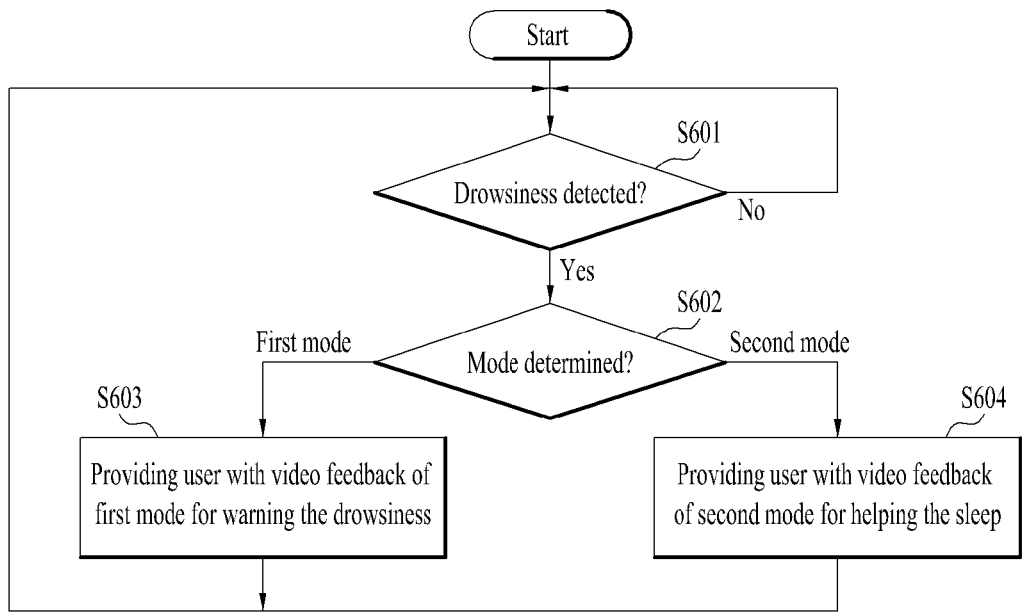
FIG. 6 is a flow chart illustrating a user interface method of the wearable computing device according to another embodiment of the present disclosure.

FIG. 6 is a flow chart of a user interface method according to a further embodiment for the wearable computing device, especially, a flow chart of a user interface when the feedback provided to the user is the video feedback.

Specifically, once the user's drowsiness is detected (S601), it is determined whether the current situation is corresponding to the first mode not allowing the drowsiness or the second mode allowing the drowsiness (S602). The method of detecting the user's drowsiness and the method of determining the mode are described in detail above and omitted accordingly.

When the current mode is determined as the first mode in the step of S602, the video feedback of the first mode for warning the drowsiness is provided to the user (S603). The message provided by the video feedback of the first mode may be the flashy photograph, painting, motion picture for fighting off the drowsiness.

When the current mode is determined as the second mode in the step of S502, the video feedback of the second mode for helping the user's sound sleep is provided to the user (S504). The message provided by the video feedback of the second mode may be the calming painting, photograph or motion picture.

Figure 7:
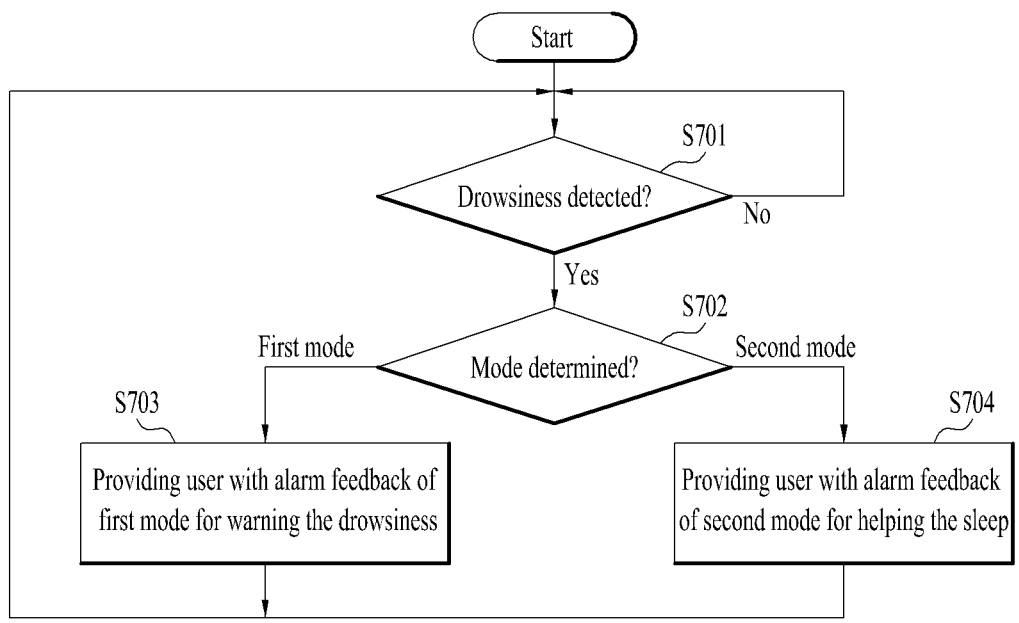
FIG. 7 is a flow chart illustrating a user interface method of the wearable computing device according to another embodiment of the present disclosure.

FIG. 7 is a flow chart illustrating a user interface according to a still further embodiment for the wearable computing device, especially, a flow chart of a user interface when the feedback provided to the user is the alarm feedback.

Specifically, once the user's drowsiness of detected (S701), it is determined whether the current situation is corresponding to the first mode not allowing the user's drowsiness or the second mode allowing the user's drowsiness (S702). The method of detecting the user's drowsiness and the method of determining the mode are described in detail above and omitted accordingly.

When the current mode is determined as the first mode in the step of S402, the alarm feedback of the first mode for warning the drowsiness is provided to the user (S703). The message provided by the alarm feedback of the first mode may be the tactile feedback which gives a stinging sensation to shake off the drowsiness.

When the current mode is determined as the second mode in the step of S702, the alarm feedback of the second mode for helping the user's sound sleep is provided to the user (S704). The message provided by the alarm feedback of the second mode may be a tactile feedback which gives a soft sensation to help the user's sound sleep.

Figure 8:
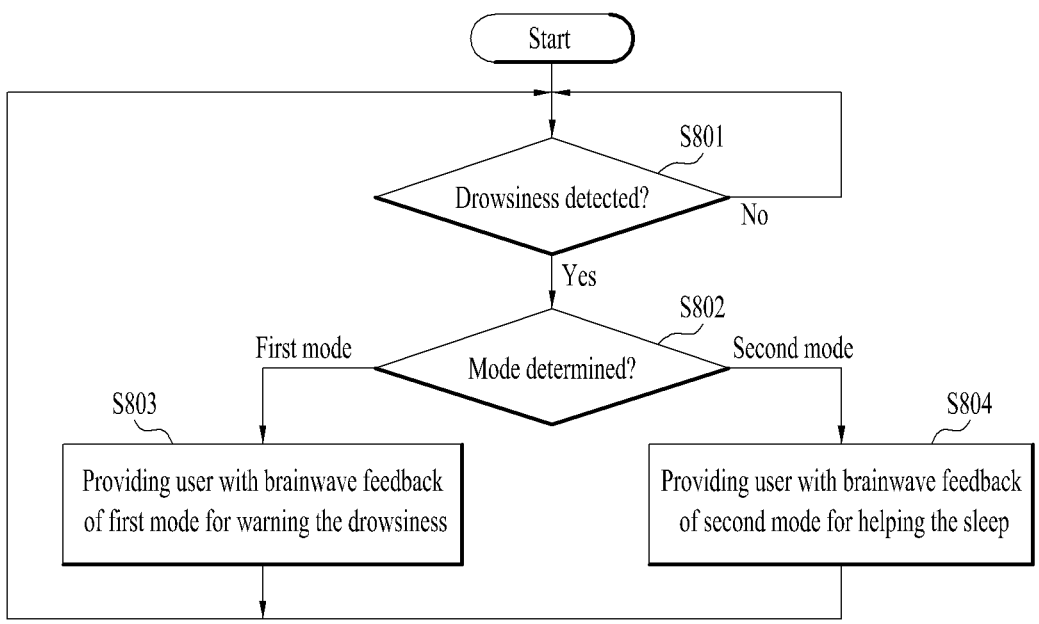
FIG. 8 is a flow chart illustrating a user interface method of the wearable computing device according to another embodiment of the present disclosure.

FIG. 8 is a flow chart illustrating a user interface according to a still further embodiment for the wearable computing device, especially, a flow chart of a user interface when the feedback provided to the user is the brainwave feedback.

Specifically, once the user's drowsiness of detected (S801), it is determined whether the current situation is corresponding to the first mode not allowing the user's drowsiness or the second mode allowing the user's drowsiness (S802). The method of detecting the user's drowsiness and the method of determining the mode are described in detail above and omitted accordingly.

When the current mode is determined as the first mode in the step of S802, the brainwave feedback of the first mode for warning the drowsiness is provided to the user (S803). The message provided by the brainwave feedback of the first mode may be the alpha wave in the frequency bandwidth range of 8 Hz~13 Hz to fight off the drowsiness.

When the current mode is determined as the second mode in the step of S802, the brainwave feedback of the second mode for helping the user's sound sleep is provided to the user (S804). The message provided by the brainwave feedback of the second mode may be the theta wave in the frequency bandwidth range of 4 Hz~7 Hz to help the sound sleep.

Figure 9:
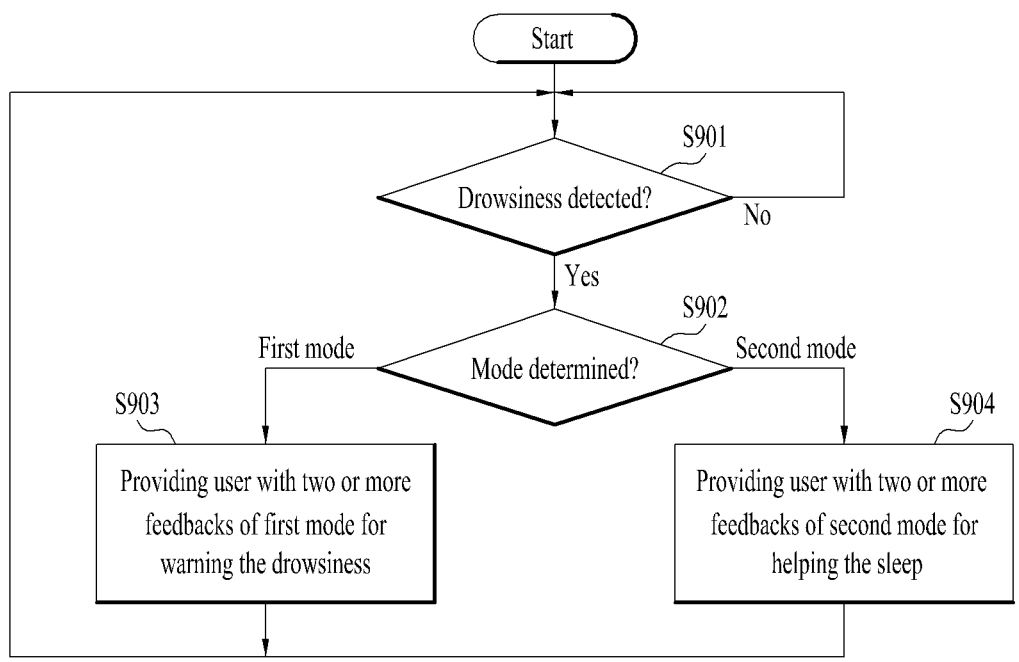
FIG. 9 is a flow chart illustrating a user interface method of the wearable computing device according to another embodiment of the present disclosure.

FIG. 9 is a flow chart illustrating a user interface according to a still further embodiment for the wearable computing device, especially, a flow chart of a user interface when two or more feedbacks are provided to the user.

Specifically, once the user's drowsiness is detected (S901), it is determined whether the current situation is corresponding to the first mode not allowing the user's drowsiness or the second mode allowing the user's drowsiness (S902). The method of detecting the user's drowsiness and the method of determining the mode are described in detail above and omitted accordingly.

When the current mode is determined as the first mode in the step of S902, two or more feedbacks of the first mode for warning the drowsiness are provided to the user (S903). The two or more feedbacks of the first mode may be two of more of the audio feedback, the video feedback, the alarm feedback and the brainwave feedback. For example, the audio feedback and the alarm feedback of the first mode may be provided to the user simultaneously. At this time, the message provided by each of the feedbacks is described in detail above and omitted accordingly.

When the current mode is determined as the second mode in the step of S902, two or more feedbacks of the second mode for helping the user's sound sleep are provided to the user (S904). The two or more feedbacks of the second mode may be two or more of the audio feedback, the video feedback, the alarm feedback and the brainwave feedback. For example, the audio feedback and the alarm feedback of the first mode may be provided to the user simultaneously. At this time, the message provided by each of the feedbacks is described in detail above and omitted accordingly.

Figure 10:
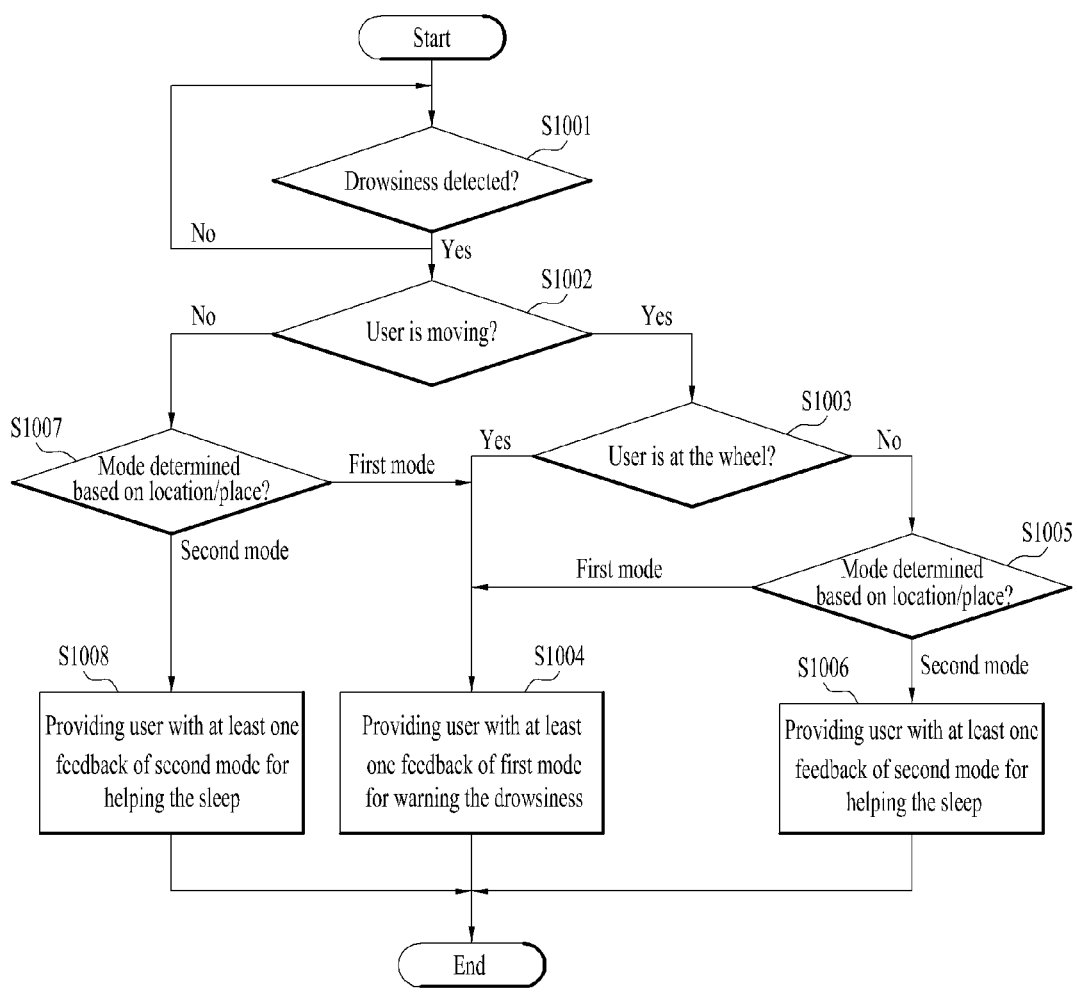
FIG. 10 is a flow chart illustrating a user interface method of the wearable computing device according to another embodiment of the present disclosure.

FIG. 10 is a flow chart illustrating a user interface according to a still further embodiment for the wearable computing device.

Specifically, once the user's drowsiness is detected (S1001), it is determined whether the user is moving (S1002). The method of detecting the user's drowsiness and the method of determining the mode are described in detail above and omitted accordingly.

When the user is moving based on the result of the determination in the step of S1002, it is determined whether the user is at the wheel (S1003). When the user is at the wheel based on the result of the determination, one or more feedbacks of the first mode are provided to the user to warn the drowsiness (S1004). The one or more feedbacks of the first mode are one or more of the audio feedback, the video feedback, the alarm feedback and the brainwave feedback. At this time, the message provided by each of the feedbacks is described in detail above and omitted accordingly.

When the user it not at the wheel based on the result of the determination in the step of S1003, it is determined whether the current situation is corresponding to the first mode or the second mode based on the user's location and/or the user's place (S1005). When the current mode is the first mode based on the result of the determination in the step of S1005, the step of S1004 is implemented and one or more feedbacks of the first mode for warning the drowsiness are provided to the user.

When the current situation is corresponding to the second mode based on the result of the determination in the step of S1005, one or more feedbacks of the second mode for helping the sound sleep are provided to the user (S1006). The one or more feedbacks of the second mode are one or more of the audio feedback, the video feedback, the alarm feedback and the brainwave feedback. At this time, the message provided by each of the feedbacks is described in detail above and omitted accordingly.

When the user is not moving based on the result of the determination in the step of S1002, it is determined whether the current situation is corresponding to the first mode or the second mode based on the user's location and/or place (S1007).

When the current mode is the first mode based on the result of the determination in the step of S1007, the step of S1004 is implemented and one or more feedbacks of the first mode for warning the drowsiness are provided to the user.

When the current mode is the second mode based on the result of the determination in the step of S1007, one or more feedbacks of the second mode for helping the sound sleep are provided to the user (S1008).

Using one or more of the images of the surrounding captured by the camera unit 223, the location information received from the GPS unit 226, the sensing information sensed by the sensor unit 225, it may be determined whether the user is moving, whether the user is at the wheel once the user is moving based on the result of the determination, whether the user is not at the wheel while moving or what is the user's current location or place once the user is not moving.

Figure 11:
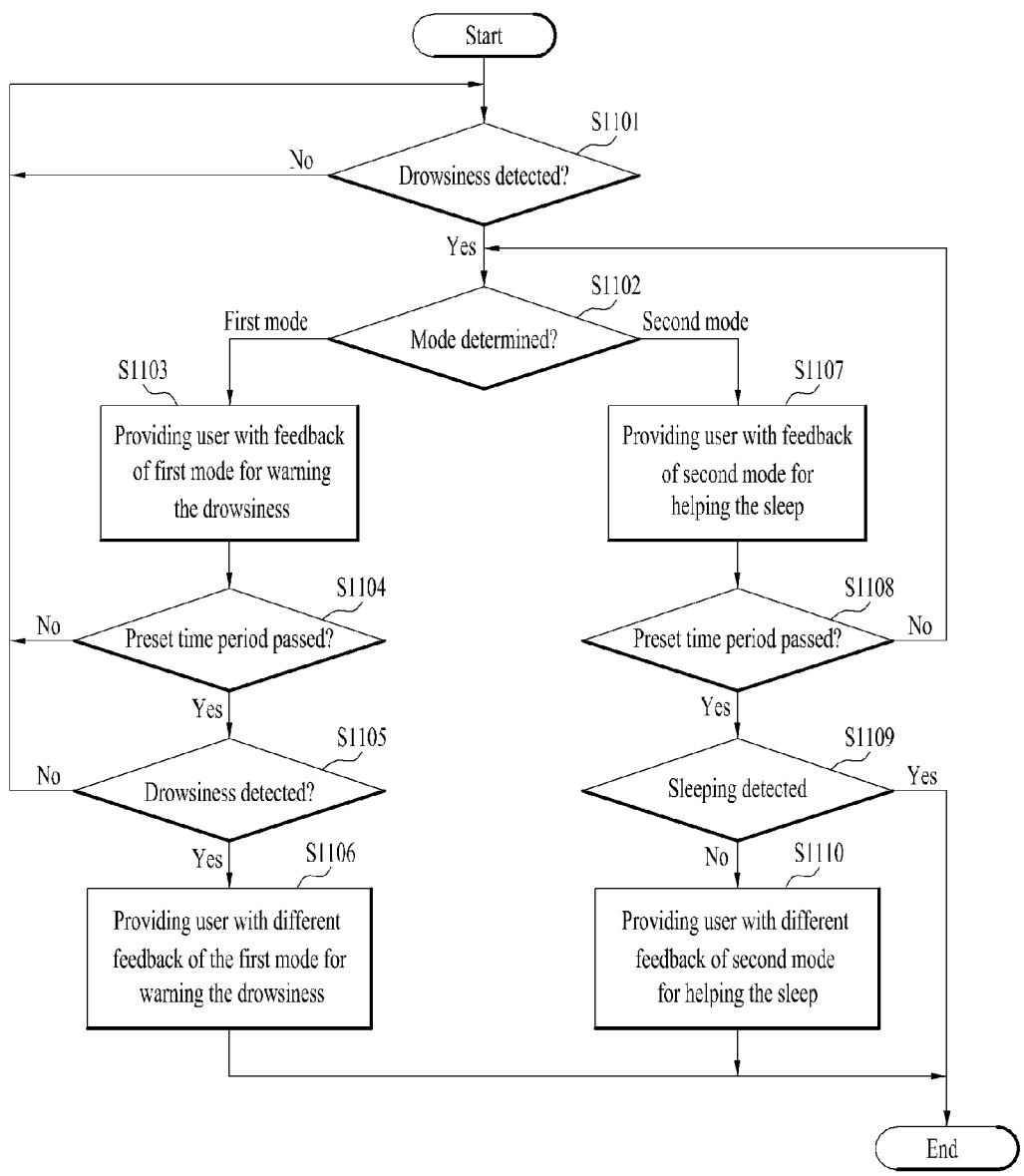
FIG. 11 is a flow chart illustrating a user interface method of the wearable computing device according to another embodiment of the present disclosure.

FIG. 11 is a flow chart illustrating a user interface according to a still further embodiment for the wearable computing device.

Specifically, once the user's drowsiness is detected (S1101), it is determined whether the current situation is the first mode not allowing the drowsiness or the second mode allowing the drowsiness (S1102). The method of detecting the user's drowsiness and the method of determining the mode are described in detail above and omitted accordingly.

When the current situation is corresponding to the first mode based on the result of the determination in the step of S1102, one or more feedbacks of the first mode for warning the drowsiness are provided to the user (S1103). The one or more feedbacks of the first mode may be one or more of the audio feedback, the video feedback, the alarm feedback and the brainwave feedback. At this time, the message provided by each of the feedbacks is described in detail above and omitted accordingly.

One a predetermined time period passes while the one or more feedbacks of the first mode are provided to the user (S1104), it is detected again whether the user is drowsy (S1105). The one or more feedbacks of the first mode may be provided to the user for a preset time period continuously or in a preset time period intermittently.

When the user's drowsiness is detected in the step of S1105, it is determined that the one or more feedbacks provided in the step of S1103 are not effective in fighting off the user's drowsiness. One or more stronger feedbacks of the first mode than those provided in the step of S1103 are provided to the user (S1106). In one embodiment, the feedback provided in S1103 may be different from the feedback provided in S1106. For example, when the feedback provided in S1103 is the audio feedback, the feedback provided in S1106 may be the brainwave feedback. In another embodiment, when the feedback provided in S1103 may be the same as the feedback provided in S1106. For example, when the feedback provided in S1103 is the audio feedback, the feedback provided in S1106 may be also the audio feedback and the message provided by the audio feedback of S1106 comprises stronger contents than the message provided by the audio feedback of S1103. For example, the message provided by the audio feedback of S1106 is the sounds of Kkwanenggari, the message provided by the audio feedback of S1103 may be sounds of rapping on a desk.

Meanwhile, when the current situation is corresponding to the second mode based on the result of the determination in S1102, one or more feedbacks of the second mode for helping sound sleep are provided to the user (S1107). The one or more feedbacks of the first mode may be one or more of the audio feedback, the video feedback, the alarm feedback and the brainwave feedback. The message provided by each of the feedbacks is described in detail above and omitted accordingly.

Once a predetermined time period passes while the one or more feedbacks of the second mode are provided to the user (S1108), it is determined whether the user is sleeping (S1109). The one or more feedbacks of the second mode may be provided to the user for a preset time period continuously or within a preset time period intermittently.

When it is detected that the user is not sleeping in S1109, it is determined that the one or more feedbacks provided in S1107 are not effective in helping the user's sound sleep. Accordingly, one or more stronger feedbacks of the second mode than the one or more feedbacks provided in S1107 are provided to the user (S1110). In one embodiment, the feedback provided in S1107 may be different from the feedback provided in S1110. For example, when the feedback provided in S1107 is the audio feedback, the feedback provided in S1110 may be the brainwave feedback. In another embodiment, when the feedback provided in S1107 may be the same as the feedback provided in S1110. For example, when the feedback provided in S1107 is the audio feedback, the feedback provided in S1110 may be also the audio feedback and the message provided by the audio feedback of S1110 comprise contents more helpful to the sound sleep than the message provided by the audio feedback of S1107. For example, the message provided by the audio feedback of S1106 is calming classic music, the message provided by the audio feedback of S1103 may be class music.

Using one of the output of the camera unit 223, the output of the sensor unit 225 and the output of the GPS unit 226, it is detected whether the user is drowsy and whether the current situation is corresponding to the first mode or the second mode. In another embodiment of the present disclosure, the first mode and the second mode may be set manually, using one or more of a button, a menu and a voice command of the wearable computing device. The feedbacks provided to the user according to the set mode may be the feedbacks mentioned above.

Meanwhile, when brightness of the lighting at the user's current location is adjustable via a communication unit 222 of the wearable computing device 220, the lighting may be brighter to fight off the user's drowsiness in the first mode and the lighting may be darker to help the user's sleep. In one embodiment, the current mode may be converted into a standby mode of the wearable computing device 220 in the second mode to help the user's sleep.

As mentioned above, the wearable computing device according to the embodiments of the present disclosure may detect whether the user is drowsy or sleepy and determines whether the current situation allows the drowsiness or not, when the user's drowsiness is detected. When the current situation is the drowsiness-not-allowing situation, the controller may provide the user with the warning feedback. When the current situation is corresponding to the drowsiness allowing situation, the controller may provide the user with the sleep-helpful feedback. In the situation not allowing the drowsiness, the wearable computing device may help the user fight off the drowsiness. In the situation allowing the drowsiness, the wearable computing device may help the user sleep sound. Especially, the driving while drowsy may be prevented and a rate of traffic accidents caused by the driving while drowsy can be lowered.

Various variations and modifications of the refrigerator described above are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A wearable computing device comprising:
  a drowsiness detection unit configured to detect a user's drowsiness;
  a camera unit configured to capture images in a range corresponding to the user's line of vision and/or images of the user's surroundings, using one or more cameras;
  a controller configured to determine whether the user is driving based on the images captured by the camera unit and determine whether a current situation corresponds to a first mode not allowing the user's drowsiness or a second mode allowing the user's drowsiness when the user's drowsiness is detected, wherein a situation when the user is driving corresponds to the first mode; and
  a feedback output unit configured to provide the user with at least one feedback comprising a message of the first mode or the second mode according to the mode determined by the controller,
  wherein the message of the first mode is to fight off the drowsiness and wherein the message of the second mode is to help the user's sleep.

2. The wearable computing device according to claim 1, wherein the drowsiness detection unit detects the user's drowsiness, using at least one of the user's eye blinking, the user's eye closing time, a state of the user's eyes, the user's pulsation, the user's brainwave, the user's body temperature and a line of the user's vision.

3. The wearable computing device according to claim 1, further comprising:
  a Global Positioning System (GPS) unit configured to receive location information of the wearable computing device from one or more GPSs.

4. The wearable computing device according to claim 3, wherein the controller determines whether the user is driving using the location information received from the GPS unit and information sensed by one or more sensor.

5. The wearable computing device according to claim 4, wherein the controller detects the user's location and place using one or more of the images captured by the camera unit, the location information received from the GPS unit and the information sensed by one or more sensors when the user is not driving based on the result of the determination, and the controller determines whether the current situation corresponds to the first mode or the second mode based on the detected location and place.

6. The wearable computing device according to claim 1, wherein the first mode and the second mode are set manually using at least one of a button, a menu and a voice command provided in the wearable computing device.

7. The wearable computing device according to claim 1, wherein the at least one feedback comprising the message of the first mode comprises at last one of a first audio feedback, a first alarm feedback, a first video feedback and a first brainwave feedback, and
  wherein the at least one feedback comprising the message of the second mode comprises at least one of a second audio feedback, a second alarm feedback, a second video feedback and a second brainwave feedback.

8. The wearable computing device according to claim 7, wherein the feedback output unit comprises:

an audio output unit configured to output one of the first audio feedback and the second audio feedback based on the control of the controller;

an alarm output unit configured to output one of the first alarm feedback and the second alarm feedback based on the control of the controller;

a display unit configured to output one of the first video feedback and the second video feedback based on the control of the controller; and a brainwave output unit configured to output one of the first brainwave feedback and the second brainwave feedback based on the control of the controller.

9. The wearable computing device according to claim 7, wherein the first brainwave feedback is an alpha wave and the second brainwave is a theta wave.

10. The wearable computing device according to claim 1, wherein the feedback provided to the user by the feedback output unit to fight off the drowsiness and the message of the first mode included in the feedback are determined by learning of the wearable computing device.

11. The wearable computing device according to claim 1, wherein the feedback provided to the user by the feedback output unit to fight off the drowsiness and the message of the first mode included in the feedback are determined by the user.

12. The wearable computing device according to claim 1, wherein the feedback provided to the user by the feedback output unit to help the user's sleep and the message of the second mode included in the feedback are determined by learning of the wearable computing device.

13. The wearable computing device according to claim 1, wherein the feedback provided to the user by the feedback output unit to help the user's sleep and the message of the second mode included in the feedback are determined by the user.

14. The wearable computing device according to claim 1, wherein the controller controls a brightness of lighting near the user based on whether the current situation corresponds to the first mode or the second mode, using a wireless communication function.

15. The wearable computing device according to claim 1, wherein the controller converts a mode of the wearable computing device into a standby mode when the current situation corresponds to the second mode.

16. The wearable computing device according to claim 1, wherein the controller provides the user with a feedback comprising a different message of the first mode when the user's drowsiness is detected after the feedback comprising the message of the first mode is provided to the user for a preset time period.

17. The wearable computing device according to claim 1, wherein the controller provides the user with a feedback comprising a different message of the second mode, when the user's sleep is not detected after the feedback comprising the message of the second mode is provided to the user.

18. The wearable computing device according to claim 1, wherein the controller provides the user with the feedback comprising the message of the second mode when a mode conversion is requested by the user while the feedback comprising the message of the first mode is provided to the user.

19. The wearable computing device according to claim 1, wherein the controller provides the user with the feedback comprising the message of the first mode when a mode conversion is requested by the user while the feedback comprising the message of the second mode is provided to the user.

20. A method of a user interface for a wearable computing device, the method comprising:

detecting whether a user is drowsy;

capturing images in a range corresponding to the user's line of vision and/or images of the user's surroundings, using one or more cameras;

determining whether the user is driving based on the images captured by the one or more cameras;

determining whether a current situation corresponds to a first mode not allowing the user's drowsiness or a second mode allowing the user's drowsiness when the user's drowsiness is detected, wherein a situation when the user is driving corresponds to the first mode; and providing the user with at least one feedback comprising a message of the first mode or the second mode according to the mode determined in the step, wherein the message of the first mode is to fight off the drowsiness and wherein the message of the second mode is to help the user's sleep.

* * * * *